(12) United States Patent
Hartley et al.

(10) Patent No.: US 8,506,616 B2
(45) Date of Patent: Aug. 13, 2013

(54) ANCHOR WIRE ARRANGEMENT (75) Inventors: David Ernest Hartley, Subiaco (AU); Wolf Stelter, Bad Soden (DE); Michael Lawrence-Brown, City Beach (AU)

(73) Assignee: Cook Medical Technologies LLC, Bloomington, IN (US)

( * ) Notice: Subject to any disclaimer, the term of this patent is extended or adjusted under 35 U.S.C. 154(b) by 1360 days.

(21) Appl. No.: 11/975,949

(22) Filed: Oct. 23, 2007

(65) Prior Publication Data

US 2008/0114438 A1 May 15, 2008

Related U.S. Application Data (63) Continuation-in-part of application No. 10/653,401, filed on Sep. 2, 2003, now abandoned.

(30) Foreign Application Priority Data

Sep. 2, 2002 (AU) .................................. 200295114

(51) Int. Cl.
*A61F 2/06* (2013.01)
(52) U.S. Cl.
USPC ........................................ 623/1.13; 623/1.11
(58) Field of Classification Search
USPC ................... 623/1.13, 1.14, 1.23, 1.32, 1.33, 623/1.35, 1.36, 1.11, 1.12
See application file for complete search history.

(56) References Cited

U.S. PATENT DOCUMENTS

| | | | |
|---|---|---|---|
| 5,387,235 A | 2/1995 | Chuter | |
| 5,554,183 A * | 9/1996 | Nazari | 623/1.49 |
| 5,676,697 A * | 10/1997 | McDonald | 623/1.35 |
| 5,693,083 A * | 12/1997 | Baker et al. | 623/1.11 |
| 5,720,776 A | 2/1998 | Chuter et al. | |
| 6,183,504 B1 * | 2/2001 | Inoue | 623/1.11 |
| 6,206,931 B1 | 3/2001 | Cook et al. | |
| 6,210,422 B1 | 4/2001 | Douglas | |
| 6,478,813 B1 * | 11/2002 | Keith et al. | 623/1.11 |
| 6,537,284 B1 * | 3/2003 | Inoue | 606/108 |
| 2001/0049550 A1 * | 12/2001 | Martin et al. | 623/1.13 |
| 2002/0007208 A1 * | 1/2002 | Strecker | 623/1.12 |
| 2002/0040236 A1 * | 4/2002 | Lau et al. | 623/1.12 |
| 2002/0151953 A1 * | 10/2002 | Chobotov et al. | 623/1.11 |

FOREIGN PATENT DOCUMENTS

| | | |
|---|---|---|
| AU | PS3215 | 6/2002 |
| AU | PS3243 | 6/2002 |
| AU | PS3244 | 6/2002 |
| AU | 2002950950 | 8/2002 |
| WO | 9809584 A1 | 3/1998 |
| WO | 98/5376 A1 | 12/1998 |
| WO | 9929262 A1 | 6/1999 |

(Continued)

*Primary Examiner* — Ryan Severson
*Assistant Examiner* — David Eastwood
(74) *Attorney, Agent, or Firm* — Richard J. Godlewski (57) ABSTRACT

An endoluminal stent graft deployment system incorporating an anchor wire system for temporary anchoring of a stent graft on a delivery device. The anchor wire system has an anchor wire extending from the distal end of the device and releasably retained to the portion of the stent graft by a releasable retention system. The releasable retention system includes a bead on the proximal end of the anchor wire and an anchor release wire which has fastening arrangement to retain the release wire distally of the bead. The anchor release wire extends to a distal end of the deployment system so that the anchor wire release wire can be withdrawn thereby releasing the anchor wire.

10 Claims, 7 Drawing Sheets

(56) References Cited

FOREIGN PATENT DOCUMENTS

| WO | 0239888 | A2 | 5/2002 |
| WO | 03034948 | A1 | 5/2003 |
| WO | 03053287 | A1 | 7/2003 |

\* cited by examiner

ANCHOR WIRE ARRANGEMENT

RELATED APPLICATIONS

This application is a continuation-in-part of U.S. patent application Ser. No. 10/653,401, filed Sep. 2, 2003 which claims priority to the Australian Provisional Patent Application Serial No. 200295114, filed Sep. 2, 2002.

TECHNICAL FIELD

This invention relates to a bifurcated or branched stent graft and to a deployment device for deploying a branched stent graft and a method of deploying such a device as well as to a temporary stent graft anchoring system.

BACKGROUND OF THE INVENTION

The invention will be generally discussed with reference to deploying a branched stent graft into an internal iliac artery from the common iliac but is not so limited and may be used with deployment into any branched vessel but is particularly applicable where the vessel into which the device is deployed is a blind vessel, that is, access is not available from an end of the vessel remote from the bifurcation from a main vessel.

Throughout this specification the term 'distal' with respect to a portion of the vasculature of a patient, a deployment device or a prosthesis is the end of the vasculature, deployment device or prosthesis furthest away in the direction of blood flow from the heart and the term 'proximal' means the portion of the vasculature, deployment device or end of the prosthesis nearer to the heart. For other lumens within the human or animal body the terms caudal and cranial respectively should be understood.

SUMMARY OF THE INVENTION

In one form the invention comprises an endoluminal stent graft deployment device in combination with a stent graft retained thereon, the device including a distal end to remain outside a patient in use and a proximal end to be deployed endoluminally into a patient and the stent graft releasably retained on the device towards the proximal end thereof, the device comprising an anchor wire arrangement to enable anchoring of a portion of the stent graft, the anchor wire arrangement comprising an anchor wire extending from the distal end of the device and releasably retained to the portion of the stent graft by a releasable retention system, the releasable retention system including a bead on the proximal end of the anchor wire, an anchor release wire and an fastening arrangement to retain the release wire distally of the bead, the anchor release wire extending to the distal end of the device, whereby the anchor wire release wire can be withdrawn thereby releasing the anchor wire.

Preferably the fastening arrangement comprises a suture fastened through the portion of the stent graft and around the anchor wire distal of the bead and retained by a knot which is locked by the anchor release wire, the anchor release wire extending to the distal end of the device, whereby the anchor wire release wire can be withdrawn from the knot thereby releasing the suture and hence the anchor wire.

Alternatively the fastening arrangement comprises a first stitch of the release wire through a portion of the stent graft on one side of the anchor wire just distal of the bead and a second stitch of the release wire through a portion of the stent graft on the other side of the anchor wire just distal of the bead such that a portion of the release wire passes over the anchor wire.

There may be further included an anchor wire catheter and wherein the anchor wire and the anchor release wire extend through the anchor wire catheter.

The bead may be crimped to the anchor wire, is soldered to the anchor wire or be a blob of solder on the anchor wire.

In an alternative form the invention comprises an endoluminal stent graft deployment device in combination with a stent graft retained thereon, the device including a distal end to remain outside a patient in use and a proximal end to be deployed endoluminally into a patient and the stent graft releasably retained on the device towards the proximal end thereof, the device comprising an anchor wire arrangement to enable anchoring of a portion of the stent graft, the anchor wire arrangement comprising an anchor wire extending from the distal end of the device and releasably retained to the portion of the stent graft by a releasable retention system, the releasable retention system including a bead on the proximal end of the anchor wire, a suture fastened through the portion of the stent graft and around the anchor wire distal of the bead and retained by a knot which is locked by an anchor wire release wire, the anchor release wire extending to the distal end of the device, whereby the anchor wire release wire can be withdrawn from the knot thereby releasing the suture and hence the anchor wire.

In an alternative form therefore the invention is said to reside in an endoluminal stent graft deployment system adapted for deployment of a limb of a branched stent graft into a blind vessel, the deployment system including, a deployment device having a distal end and a proximal end and including the branched stent graft releasably retained thereon at the proximal end thereof, an inner sheath slidably and coaxially mounted on the deployment device, the branched stent graft having a main body and a limb extending therefrom, the limb extending distally from a bifurcation in the main body, the branched stent graft being mounted on the deployment device with the deployment catheter passing through the main body, the inner sheath enclosing the main body up to distally of the bifurcation, and a separate deflecting wire guide extending into the limb from the distal end of the deployment device.

Preferably the endoluminal stent graft deployment device further includes an outer sheath slidably and coaxially mounted on the inner sheath and adapted to enclose the entire stent graft.

Preferably the endoluminal stent graft deployment system further includes an anchor wire arrangement extending between the inner and outer sheaths and extending to and fastened to the main body of the stent graft adjacent to the bifurcation.

The anchor wire arrangement may include an anchor wire and an anchor release wire and the anchor release wire extending to an anchor wire release arrangement at the distal end of the deployment device and adapted to remain outside the patient during deployment.

The separate deflecting wire guide may include a guide wire arrangement extending through the limb and extending distally therefrom to assist with directing the limb into the blind vessel.

Preferably the separate deflecting wire guide extending to the limb includes a guide wire and a guide wire sheath, the guide wire being movable within the guide wire sheath from outside the patient during deployment.

The deployment device may include a guide wire catheter mounted coaxially and movably within a deployment catheter, the guide wire catheter extending to a nose cone and the branched stent graft releasably retained distally of the nose cone.

Preferably the endoluminal stent graft deployment system further includes a diameter reducing arrangement on at least part of the main body of the stent graft and a diameter reducing arrangement on the limb of the stent graft.

The diameter reducing arrangements may each include ties around the main body or limb to reduce the diameter of the main body or limb from a deployed diameter to a compressed diameter and a trigger wire arrangement to release the ties to allow the main body or limb to expand to the deployed diameter. Generally it is intended that the released ties remain associated with the stent graft.

The trigger wire arrangement may include a trigger wire release arrangement at the distal end of the deployment device that is adapted to remain outside the patient during deployment.

In one form the branched stent graft comprises a tubular body and self expanding stents at, at least the proximal and distal ends of the main body and at the distal end of the limb. Further self expand stents may be provided on the main body and limb. The stents may be zig-zag Z stents made from Nitinol or stainless steel.

Preferably the limb includes on an outer surface thereof fibres extending therefrom to improve adhesion to the vessel wall.

The anchor wire arrangement may include an anchor wire and an anchor wire release wire and the anchor wire release wire extending to an anchor wire release arrangement at the distal end of the deployment device and adapted to remain outside the patient during deployment. The anchor wire and anchor wire release wire extend through an anchor wire catheter which is positioned between the inner and outer sheaths.

U.S. Pat. No. 5,387,235 entitled "Endovascular Transluminal Prosthesis For Repair Of Aneurysms" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Stent Barb" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

PCT Patent Publication Number No. WO98/53761 entitled "A Prosthesis and a Method of Deploying a Prosthesis" discloses an introducer for a prosthesis which retains the prosthesis so that each end can be moved independently. These features and other features disclosed in PCT Patent Publication Number No. WO98/53761 could be used with the present invention and the disclosure of PCT Patent Publication Number No. WO98/53761 is herewith incorporated in its entirety into this specification.

PCT Patent Publication Number No. WO99/29262 entitled "Endoluminal Aortic Stents" discloses a fenestrated prosthesis for placement where there are intersecting arteries. This feature and other features disclosed in PCT Patent Publication Number No. WO99/29262 could be used with the present invention and the disclosure of PCT Patent Publication Number No. WO99/29262 is herewith incorporated in its entirety into this specification.

PCT Patent Publication Number No. WO03/034948 entitled "Prostheses for Curved Lumens" discloses prostheses with arrangements for bending the prosthesis for placement into curved lumens. This feature and other features disclosed in PCT Patent Publication Number No. WO03/034948 could be used with the present invention and the disclosure of PCT Patent Publication Number No. WO03/034948 is herewith incorporated in its entirety into this specification.

Australian Provisional Patent Application Number No. PS3244 entitled "Trigger Wires" discloses release wire systems for the release of stent grafts retained on introducer devices. This feature and other features disclosed in Australian Provisional Patent Application Number No. PS3244 could be used with the present invention and the disclosure of Australian Provisional Patent Application Number No. PS3244 is herewith incorporated in its entirety into this specification.

Australian Provisional Patent Application Number No. PS3243 entitled "Thoracic Deployment Device" discloses introducer devices adapted for deployment of stent grafts particularly in the thoracic arch. This feature and other features disclosed in Australian Provisional Patent Application Number No. PS3243 could be used with the present invention and the disclosure of Australian Provisional Patent Application Number No. PS3243 is herewith incorporated in its entirety into this specification.

Australian Provisional Patent Application Number No. PS3215 entitled "A Stent-Graft Fastening Arrangement" discloses arrangements for fastening stents onto grafts particularly for exposed stents. This feature and other features disclosed in Australian Provisional Patent Application Number No. PS3215 could be used with the present invention and the disclosure of Australian Provisional Patent Application Number No. PS3215 is herewith incorporated in its entirety into this specification.

PCT Patent Publication Number No. WO03/053287 entitled "Improving Graft Adhesion" discloses arrangements on stent grafts for enhancing the adhesion of such stent grafts into walls of vessels in which they are deployed. This feature and other features disclosed in PCT Patent Publication Number No. WO03/053287 could be used with the present invention and the disclosure of PCT Patent Publication Number No. WO03/053287 is herewith incorporated in its entirety into this specification.

Australian Provisional Patent Application Number No. 2002950950 entitled "Composite Prostheses" discloses prostheses or stent grafts suitable for endoluminal deployment. These prostheses and other features disclosed in Australian Provisional Patent Application Number No. 2002950950 could be used with the present invention and the disclosure of Australian Provisional Patent Application Number No. 2002950950 is herewith incorporated in its entirety into this specification.

BRIEF DESCRIPTION OF THE DRAWING

This generally describes the invention but to assist with understanding the invention will now be exemplified with the assistance of the accompanying drawings.

In the drawings.

DETAILED DESCRIPTION

Figure 1:
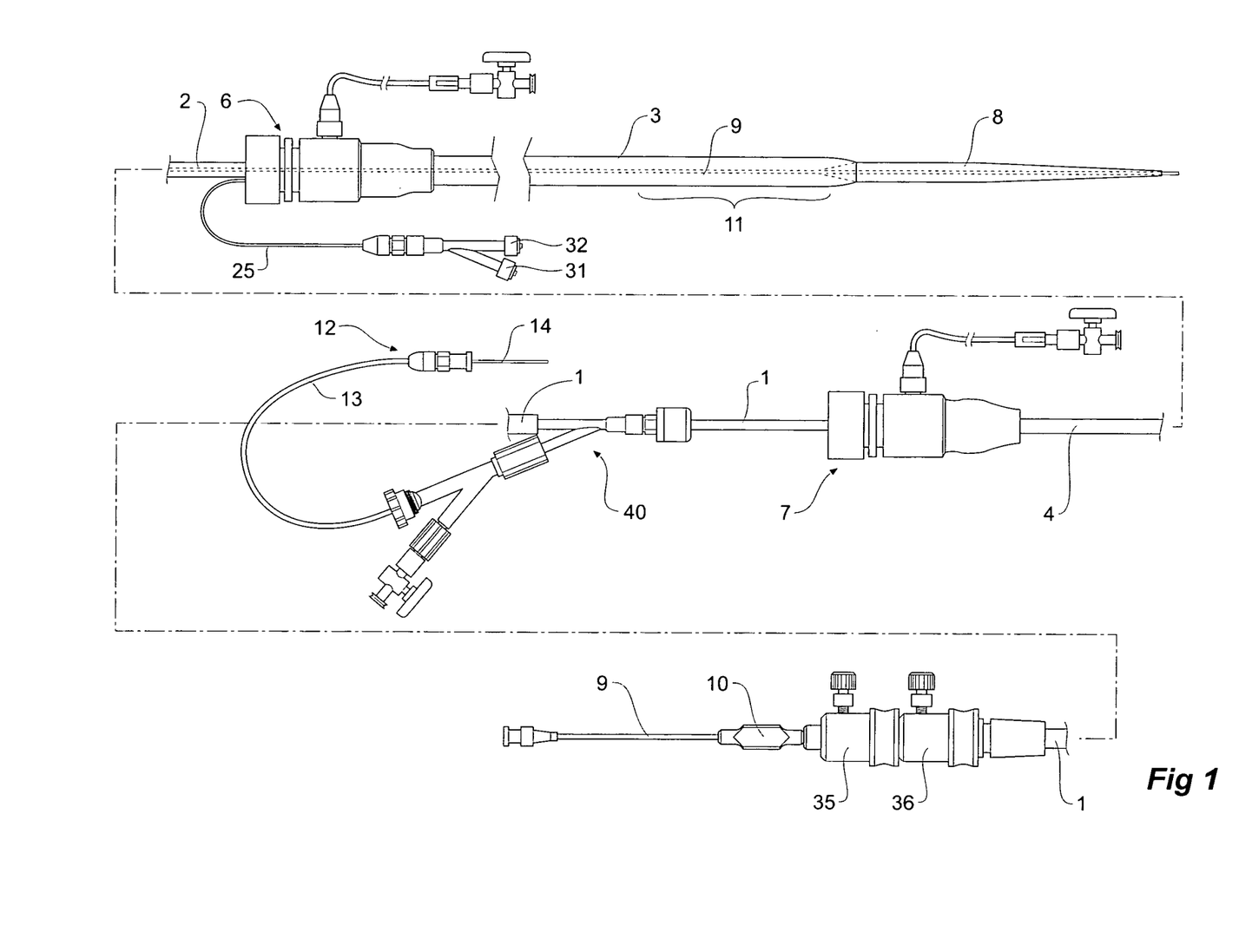
FIG. 1 shows a deployment device according to one embodiment of the invention.
Figure 2A:
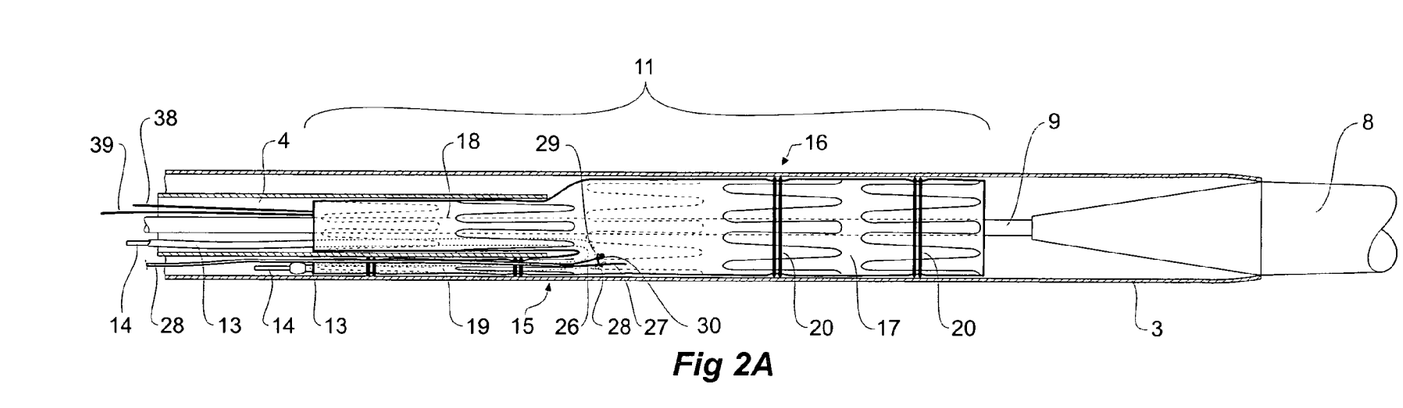
FIGS. 2A to 2I show various stages of deployment using the device shown in FIG. 1.
Figure 2B:
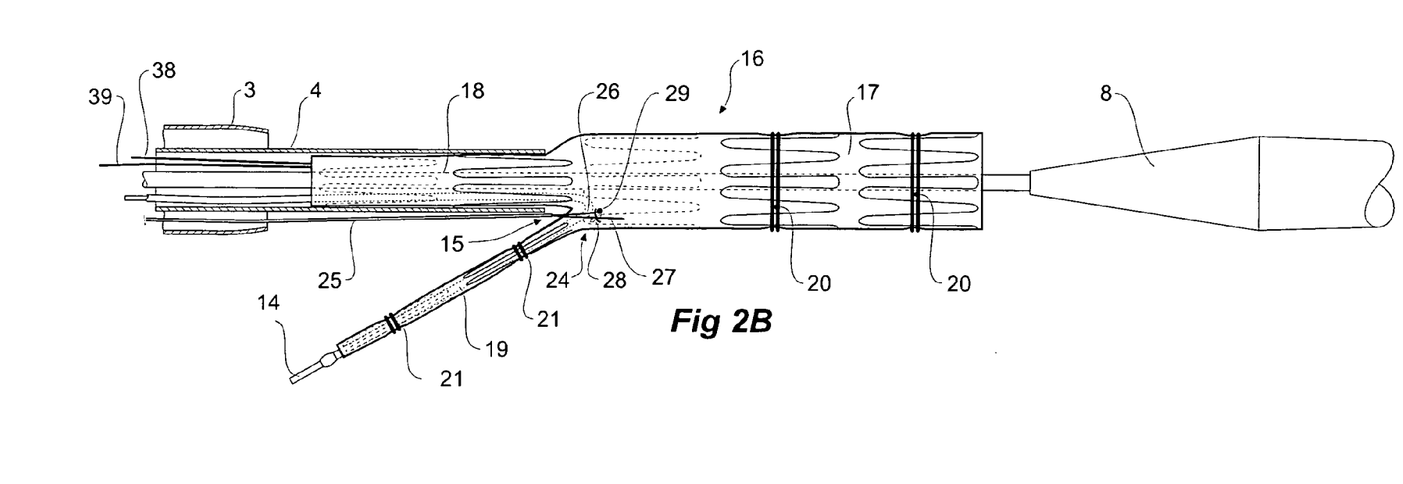

Now looking more closely at the drawings and more particularly the embodiment shown in FIG. 1 and parts of this embodiment shown in FIGS. 2A and 2B it will be seen that the deployment device comprises a deployment catheter 1 having slidably mounted over it an outer sheath 3 and an inner sheath 4. The outer sheath 3 is manipulated from an outer sheath manipulator generally shown as 6 and the inner sheath is manipulated from an inner sheath manipulator 7. Extending from a nose cone 8 throughout the deployment catheter is a guide wire catheter 9. The guide wire catheter 9 is fixed for movement with respect to the deployment catheter 1 by means of a pin vice 10. Release of the pin vice allows movement of the nose cone with respect to the deployment catheter 1.

A stent graft 16 (FIG. 2A) is retained in the region 11 of the deployment device immediately distally of the nose cone 8 as can be particularly seen in FIG. 2A. The stent graft 16 includes a proximal body portion 17 enclosed and retained in a constrained state by the outer sheath 3 and a distal body portion 18 enclosed and retained in a constrained state by the inner sheath 4. Extending between the proximal 16 and distal 18 body portions from a bifurcation 15 is a limb 19. The proximal body portion 17 is retained in a compressed state by diameter reducing ties 20 and the limb 19 is retained in a compressed state by diameter reducing ties 21. The method of releasing these diameter reducing ties will be discussed later.

A deflecting wire guide arrangement generally shown as 12 on the deployment device in FIG. 1 has a guide wire catheter 13 with a guide wire 14 within it.

The separate deflecting guide wire catheter 13 extends from the deployment catheter 1 at a Y-piece generally shown as 40.

The deflecting guide wire catheter 13 extends from the part of the deployment device which in use remains outside of the patient through the inner sheath 3 and is bent and extends into the limb 19. When the limb 19 is released as discussed below the deflecting wire guide assists in causing the limb to deflect laterally from the main body of the stent graft.

An anchor wire arrangement is mounted at 24 to the main body of the stent graft 16 adjacent the bifurcation 15. The anchor wire arrangement includes an anchor wire catheter 25, an anchor wire 26 which passes through the anchor wire catheter 25 and an anchor wire release wire 27 which also passes through the anchor wire catheter 25. The anchor wire 26 includes a bead 29 at its proximal end so that a suture 30 can be fastened through the stent graft body adjacent to the bifurcation 15 and then around the anchor wire 26 and retained by a knot 28 which is locked by the anchor wire release wire 27. The anchor wire catheter 25 passes between the outer sheath 3 and the inner sheath 4 and extends out of the rear of the outer sheath manipulator 6. The cap 32 can be removed to enable release of the anchor wire release wire 27 and pull it through the anchor wire catheter 25 and the cap 31 can be released to pull the actual anchor wire 26 back. When the anchor wire release wire 27 is withdrawn the knot 28 is unlocked and the suture 30 is released and the anchor wire 26 is released from the stent graft body 16.

The diameter reducing ties 21 on the limb 19 are activated by the release of the trigger wire mechanism 35 on the deployment catheter 1. The diameter reducing ties 20 on the proximal body portion 17 are released by means of the trigger wire release mechanism 36. Trigger wire 38 extends from the diameter reducing ties 20 to the release 36 and trigger wire 39 extends from the diameter reducing ties 21 to the release 35.

This then generally describes the deployment apparatus but to assist with understanding reference will now be made to FIGS. 2A to 2I which show various stages of deployment of a stent graft using the deployment device discussed in relation to FIG. 1.

In FIG. 2A it will be seen that the stent graft 16 is retained within the outer sheath 3 and inner sheath 4 in the manner discussed above. It will be noted that the limb 19 is outside the inner sheath 4 but inside the outer sheath 3.

In FIG. 2B the outer sheath has been withdrawn to allow the limb 19 to deflect laterally.

For clarity the portion of the iliac bifurcation into which the device is deployed according to this invention is not illustrated in FIGS. 2A and 2B but is shown in dotted lines in later illustrations.

Figure 2C:
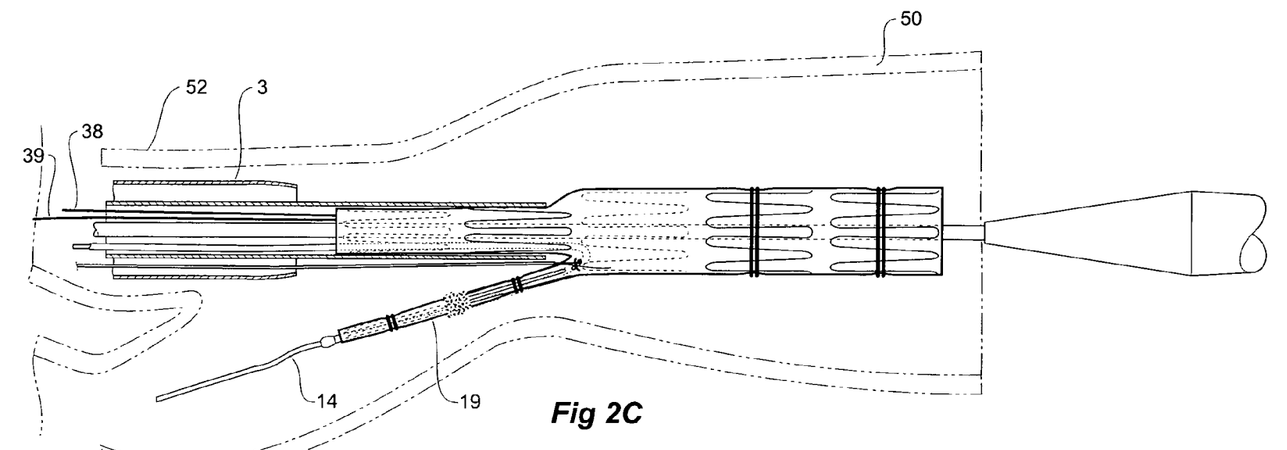

As can be seen in FIG. 2C, the deployment device is deployed in an iliac artery which has a common iliac artery 50 branching into an internal iliac artery 51 and the external iliac artery 52. The deployment device has been deployed through the external iliac artery 52. The common iliac artery 50 is deformed into an aneurysmal sac and to provide a good place for deployment of a leg of an endoluminal device to bridge the aneurysm the device of the present invention is deployed.

As can be seen in FIG. 2C, the outer sheath 3 has been withdrawn to a position in which where the limb 19 can escape from being retained by the outer sheath 3 and the guide wire 14 has been advanced so that it can extend into the internal iliac artery 51. It will be understood by those skilled in the field that radiological techniques can be used to ensure proper alignment before advancement of the guide wire 14 into the internal iliac artery 51. Suitable radiopaque markers may be place as needed on the main body and limb to assist with placement and contrast fluids may be provided through the deployment device to assist with visualization of the arterial structure.

Figure 2D:
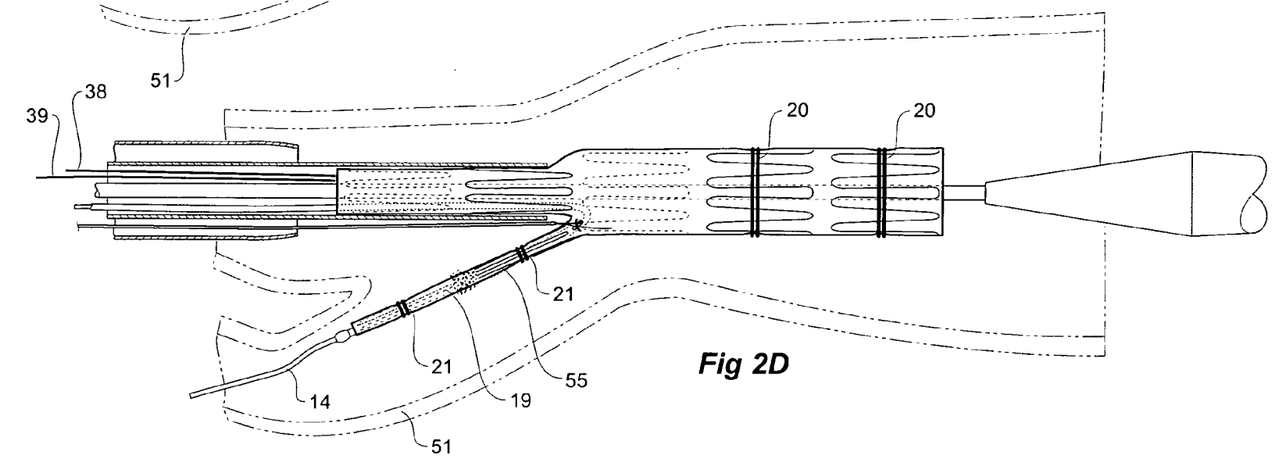

As can be seen in FIG. 2D, once the guide wire 14 has been deployed into the internal iliac artery 51, the entire device can be manipulated from outside the patient by being withdrawn slightly so that the limb 19 extends into the internal iliac artery 51 while being guided by the already placed guide wire 14.

Figure 2E:
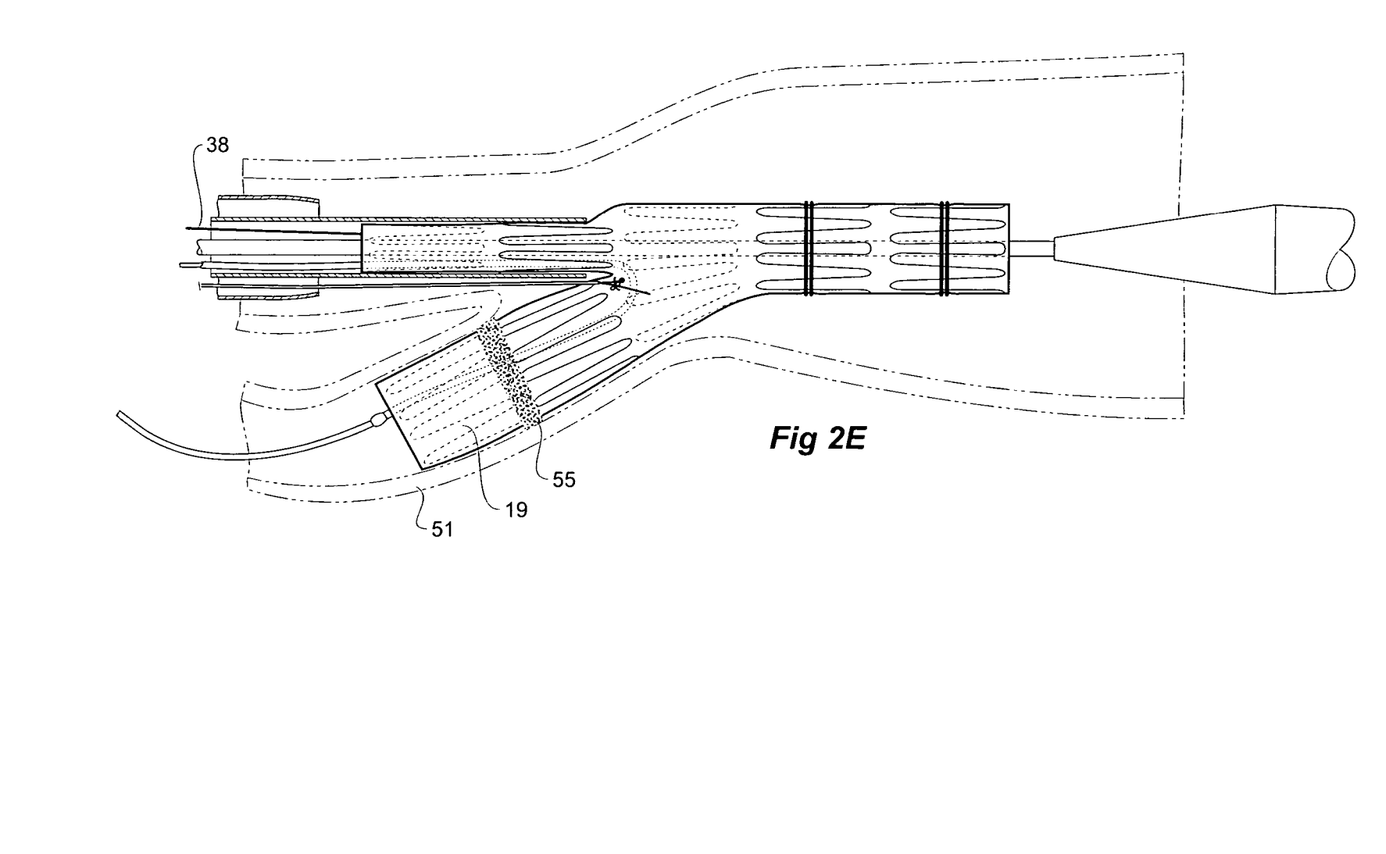

Once a sufficient amount of the limb has been deployed into the internal iliac artery 51, which can be observed by suitable radiological techniques, the diameter reducing ties 21 on the limb 19 are released by removal of the trigger wire release 35 and the limb 19 expands under the effect of self expanding stents to engage with the walls of the internal iliac 51 as particularly can be seen in FIG. 2E. It will be noted that fibres 55 are included on the limb 19 to improve adhesion onto the wall of the internal iliac artery 51 by encouraging ingrowth.

Figure 2F:
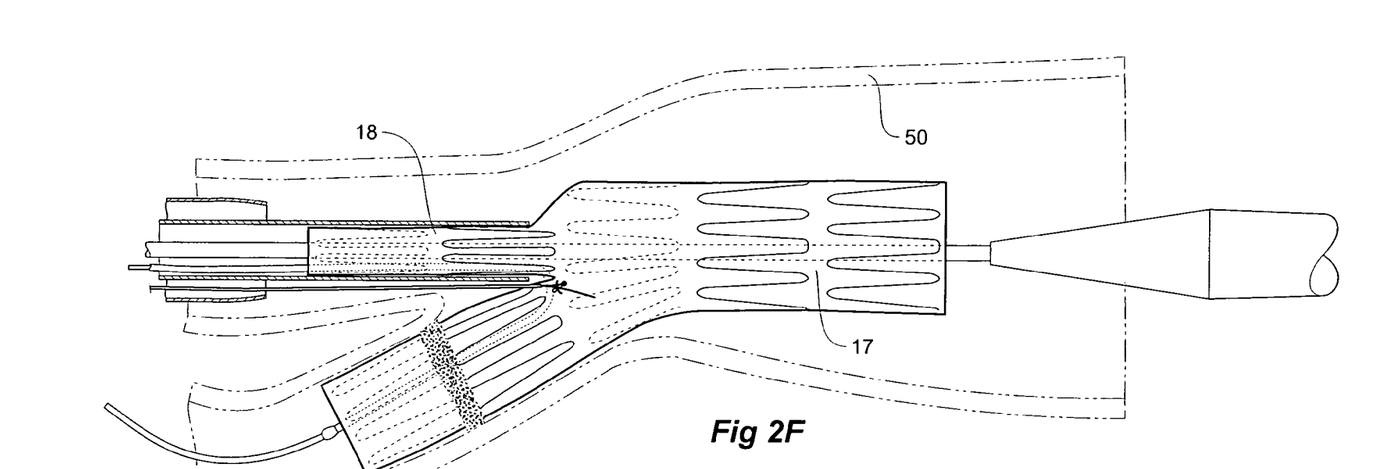

As can be seen in FIG. 2F, the diameter reducing ties 20 on the proximal body portion 19 have been released by removal of the trigger wire release mechanism 36 so that the proximal body portion expands under the effect of self expanding stents to its full size. At this stage, however, the proximal body portion does not necessarily engage with the walls of the common iliac artery 50 because of the aneurysmal sac within the vessel 50.

Figure 2G:
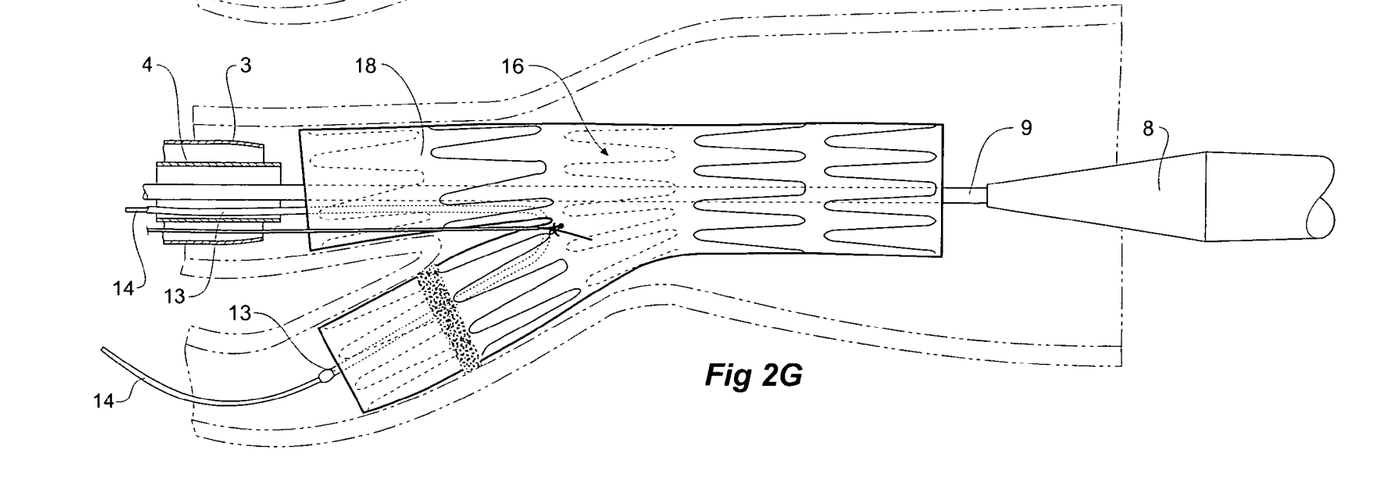

In the next stage, as shown in FIG. 2G, the inner sheath 4 is withdrawn to release the distal body portion 18 which expands under the effect of self expanding stents to engage against the walls of the external iliac artery. At this stage the deployment of the iliac branched stent graft is essentially completed and the nose cone 8, guide wire catheter 9 and internal sheath 4 along with the separate guide wire catheter 13 and guide wire 14 can be withdrawn leaving the outer sheath 3 in place for deployment of other devices through the iliac branched stent graft 16 as required. At this stage, however, the anchor wire arrangement may still be maintained in place to hold the branched stent graft in place while further deployment occurs through the device.

Deployment of subsequent devices can be carried out over guide wire 57 which remains in place after removal of the iliac branched stent graft deployment device.

Figure 2H:
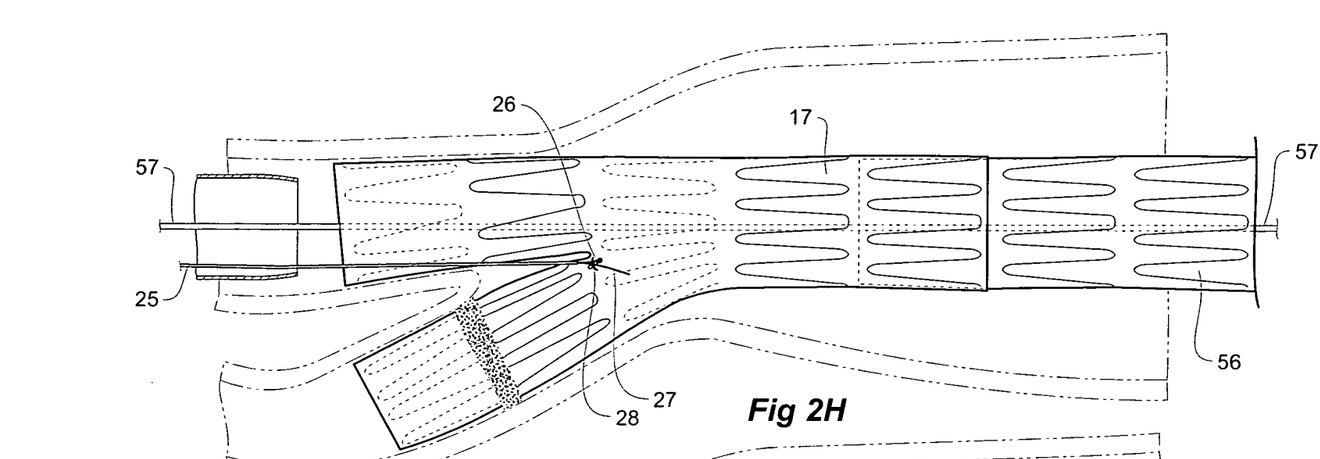

FIG. 2H for instance shows the leg 56 of a further stent graft deployed within the proximal end of the proximal body portion 17.

Figure 2I:
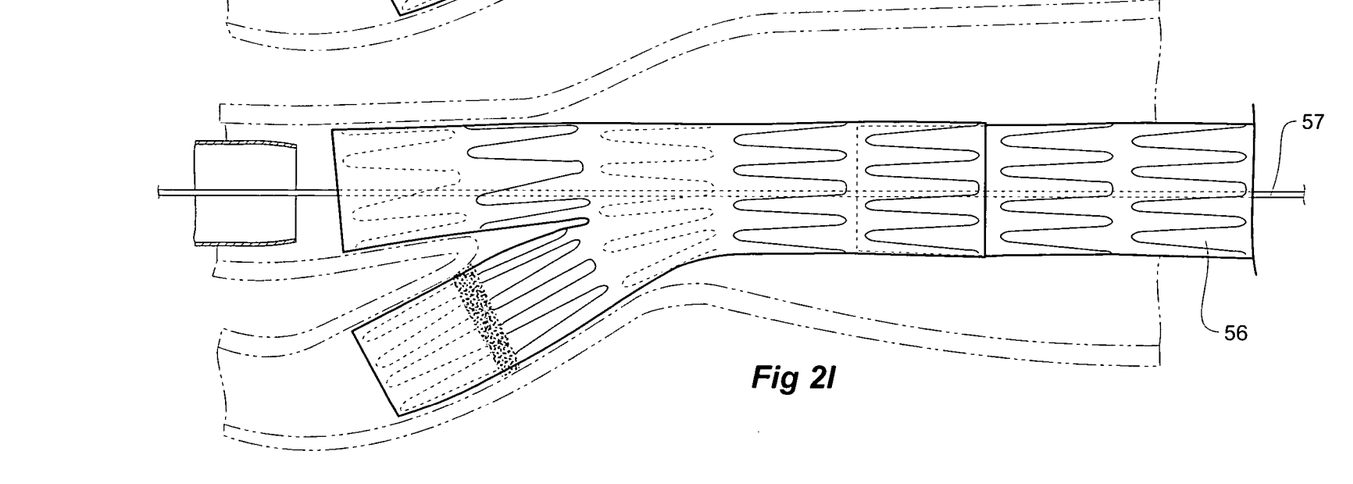

After deployment of further stent grafts as required, the anchor wire arrangement can be withdrawn by withdrawal of the anchor wire release wire 27 which releases the knot 28 so that the anchor wire 26 and the anchor wire catheter 25 can be then be withdrawn to leave the situation shown in FIG. 2I.

It will be seen generally by this invention that a stent graft can be deployed into a blind vessel such as an internal iliac and then that stent graft anchored while further stent grafting is occurring.

Figure 3:
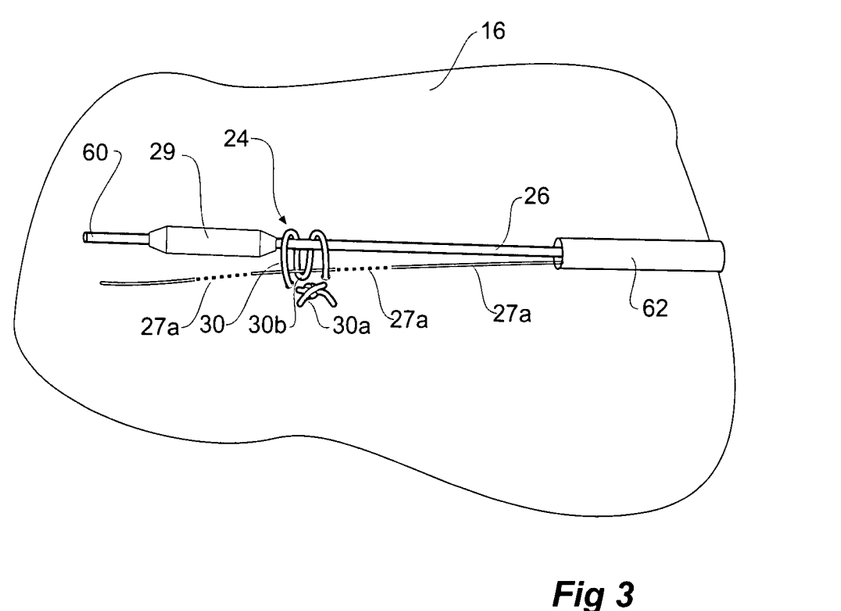
FIG. 3 shows detail of an anchor wire system according to the present invention.

FIG. 3 shows detail of an anchor wire retention system 24 by which an anchor wire 26 can be joined to a stent graft so that the stent graft can be held in a selected position during a movement which would otherwise undesirably move the stent graft.

The anchor wire 26 has a bead 29 which is soldered or crimped onto the anchor wire towards its proximal end 60. Alternatively the bead may be a blob of solder on the anchor wire. The anchor wire 26 is laid along the graft material 16 and a suture 30 is fastened around the anchor wire distally of the bead 29 with a loop 30b around an anchor release wire 27 which is stitched through the material of the stent graft 16 at 27a and 27 b and then the suture 30 is sewn at 30a into the graft material 16. When the release wire 27 is retracted the loop 30b of the suture 30 is released and the anchor wire 26 can be retracted. With the suture 30 fastened the bead 29 cannot be withdrawn through the suture.

In one embodiment the anchor wire 26 and the release wire may be retained within an anchor wire catheter 62 distally of the arrangement 24.

Figure 4:
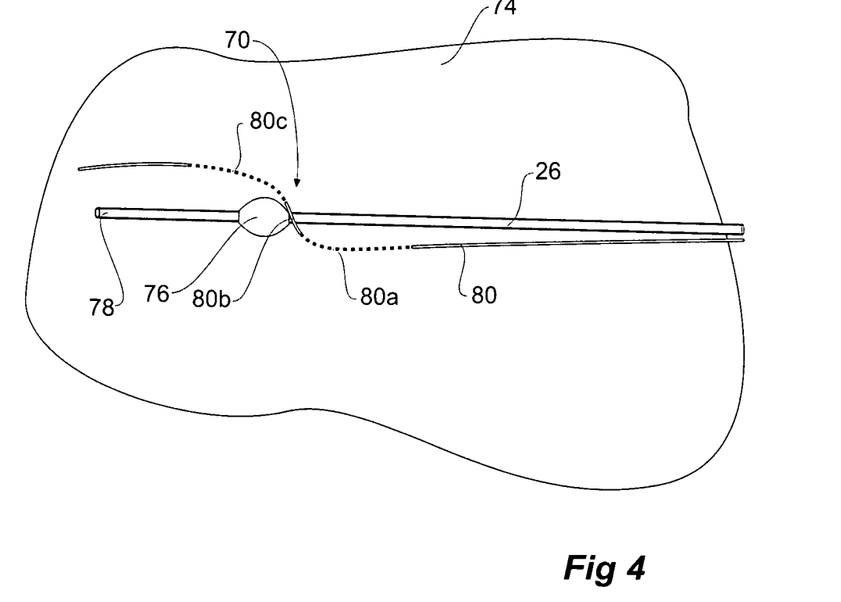
FIG. 4 shows detail of an alternative anchor wire system according to the present invention.

FIG. 4 shows detail of an alternative anchor wire retention system 70 in which an anchor wire 72 can be joined to a stent graft material 74 so that the stent graft can be held in a selected position during a movement which would otherwise undesirably move the stent graft.

The anchor wire 72 has a bead 76 thereon towards its proximal end 78. In this embodiment the bead 76 is a blob of solder on the anchor wire. The anchor wire 72 is laid along the graft material 74 and an anchor release wire 80 is stitched through the graft material at 82a just distal of and adjacent to the bead 76 and then passed over the anchor wire 72 as at 82b and then stitched through the graft material at 82c. By this arrangement the anchor wire is locked in place.

The use of an anchoring system using an anchor wire and an anchor wire release is not restricted to this application but may be used in other situations where a temporary anchoring of a stent graft is desirable.

Throughout this specification various indications have been given as to the scope of the invention but the invention is not limited to only one of these but may reside in two or more of these combined together. The examples are given for illustration only and not for limitation.

What is claimed is:

1. An endoluminal stent graft deployment device in combination with a stent graft retained thereon, the device including a distal end to remain outside a patient in use and a proximal end to be deployed endoluminally into a patient and the stent graft releasably retained on the device towards the proximal end thereof, the device comprising an anchoring arrangement, the anchoring arrangement enabling anchoring of a portion of the stent graft, the anchoring arrangement comprising an anchor wire extending from the distal end of the device and the anchor wire being releasably retained to the portion of the stent graft by a releasable retention system, the releasable retention system including a bead on the proximal end of the anchor wire, an anchor wire release wire and a fastening arrangement to retain the anchor wire to the portion of the stent graft distally of the bead, the anchor wire release wire being engaged with the fastening arrangement to prevent release of the fastening arrangement, the anchor wire release wire extending to the distal end of the device, the bead on the anchor wire configured to engage against the fastening arrangement thereby preventing the anchor wire from being released from the portion of the stent graft until the fastening arrangement is released, whereby the anchor wire release wire can be withdrawn thereby releasing the fastening arrangement and thereby the anchor wire, wherein the fastening arrangement comprises a suture fastened through the portion of the stent graft and around the anchor wire distal of the bead and retained by a knot which is locked by the anchor wire release wire, whereby the anchor wire release wire can be withdrawn from the knot thereby releasing the suture and hence the anchor wire.

2. A device as in claim 1 further including an anchor wire catheter and wherein the anchor wire and the anchor wire release wire extend through the anchor wire catheter.

3. A device as in claim 1 wherein the bead is crimped to the anchor wire.

4. A device as in claim 1 wherein the bead is soldered to the anchor wire.

5. A device as in claim 1 wherein the bead is a blob of solder on the anchor wire.

6. An endoluminal stent graft deployment device in combination with a stent graft retained thereon, the device including a distal end to remain outside a patient in use and a proximal end to be deployed endoluminally into a patient and the stent graft releasably retained on the device towards the proximal end thereof, the device comprising an anchor wire arrangement to enable anchoring of a portion of the stent graft, the anchor wire arrangement comprising an anchor wire extending from the distal end of the device and releasably retained to the portion of the stent graft by a releasable retention system, the releasable retention system including a bead on the proximal end of the anchor wire, a suture fastened through the portion of the stent graft and around the anchor wire distal of the bead and retained by a knot which is locked by an anchor wire release wire, the bead on the anchor wire is configured to engage against the suture, the anchor wire release wire extending to the distal end of the device, whereby the anchor wire release wire can be withdrawn from the knot thereby releasing the suture and hence the anchor wire.

7. An anchor wire anchoring arrangement, the anchor wire anchoring arrangement comprising an anchor wire comprising a first end and a second end and intended for anchoring the first end of the anchor wire to a graft material for prevention of movement of the anchor wire towards the second end, the anchor wire comprising a bead thereon towards the first end thereof, a suture thread fastened in a loop to the graft material immediately to the second end side of the bead, the loop of suture thread passing around the anchor wire and being engaged with a release wire which extends through the loop such that the suture thread is configured to engage the bead, whereby when the release wire is retracted from the loop of the suture thread, the loop is disengaged from around the anchor wire and the anchor wire can be moved.

8. An anchor wire anchoring arrangement as in claim 7 wherein the bead is crimped to the anchor wire.

9. An anchor wire anchoring arrangement as in claim 7 wherein the bead is soldered to the anchor wire.

10. An anchor wire anchoring arrangement as in claim 7 wherein the bead comprises a blob of solder on the anchor wire.

* * * * *